United States Patent [19]

Tomlinson

[11] 4,130,636

[45] Dec. 19, 1978

[54] DENTIFRICE

[75] Inventor: Kenneth Tomlinson, Bramhall, England

[73] Assignee: Colgate-Palmolive Company, New York, N.Y.

[21] Appl. No.: 819,528

[22] Filed: Jul. 27, 1977

[51] Int. Cl.² ............................ A61K 7/16; A61K 7/18
[52] U.S. Cl. .......................................... 424/52; 424/49; 424/56; 424/57
[58] Field of Search ....................................... 424/49–58

[56] References Cited

U.S. PATENT DOCUMENTS

| | | | |
|---|---|---|---|
| 2,359,326 | 10/1944 | Moss et al. | 424/56 |
| 2,812,284 | 11/1957 | Sanders | 424/56 |
| 3,256,155 | 6/1966 | Cahn et al. | 424/56 |
| 3,462,525 | 8/1969 | Levinsky et al. | 424/56 |
| 3,531,564 | 9/1970 | Bouchal et al. | 424/52 |
| 3,692,894 | 9/1972 | Amo et al. | 424/56 |

Primary Examiner—Shep K. Rose
Attorney, Agent, or Firm—Robert L. Stone; Murray M. Grill; Herbert S. Sylvester

[57] ABSTRACT

There is disclosed an oral product containing a new and improved surfactant system that is non-toxic, edible and surprising substantially tasteless.

14 Claims, No Drawings

DENTIFRICE

This invention relates to an improved dentifrice preparation; more particularly, to a dentifrice having a substantially tasteless surfactant. It has repeatedly been stated that taste and flavor are perhaps the most important single aspects with respect to the consumer acceptance of an oral product. The selection of acceptable ingredients is therefore of paramount importance in the formulation of the product. It has oftentimes been stated that the foregoing is both an art as well as a science. It is an art in the sense that it requires the blending of the various components such that the final composition contains a pleasing taste as well as in providing for a composition in which the various ingredients are stable. Taste has presented particular difficulties in oral products and especially the taste associated with the surfactant that is almost always of necessity found in an oral product. The undesirable taste of the surfactant is an important considerations in formulations, due to the fact that the same is almost a necessity in a commercially acceptable product, the formulator must work around the taste imparted to the product by virtue of the surfactant. This is generally difficult and adds an additional formulation and taste factor to the product that further complicates the processing.

Generally speaking, all commercially available surfactants for use in an oral product have a bitter taste associated therewith. This property necessitates the use of a sweetener further complicates matters in that the same should be non-cariogenic, exhibit sufficient sweetness at low levels of use and be compatible with the remainder of the oral product constituents.

At the present time, there are a relatively few sweeteners which are both currently available for use in a dentifrice as well as generally acceptable for use therein. One of the better known sweeteners is saccharin, however, its use may present some difficulties and oftentimes, when used as the sole sweetener, it too leaves a bitter taste. Other more exotic sweeteners though available, are generally not acceptable for use in the dentifrice due to their stability problems vis-a-vis the various components in the dentifrice. Some of those sweeteners which do not have stability problems have the drawback that they are not suitable for use as a primary sweetener due to the unacceptable timelag prior to the onset of their sweetness and/or their associated side tastes. The sweetener employed must have the quality of a rapid onset of sweetness so as to mask the generally bitter flavor associated with detergent-like ingredients. The use of low intensity sweeteners is, therefore, not practical for use in most dentifrice formulations. Merely increasing the amount of low intensity sweetener so as to overcome the foregoing deficiencies does not prove very helpful inasmuch as a dentifrice generally contains large amounts of humectants, polishing agents, water and the like and therefore from a volume point of view, it is not practical.

A further consideration in formulating a dentifrice relates to the fact that the polishing agents employed therein are generally absorbent materials and therefore there may be a selective absorption onto the polishing agent of the sweetener with accompanying change in physical form of the toothpaste, chemical changes and resultant overall flavor.

This invention accordingly is directed to alleviating the problems referred to above by providing for a surfactant that is compatible and efficacious, does not exhibit a bitter taste, and if desired, allows one to formulate an oral product without the use of a sweetener ordinarily needed to mask the surfactant taste. Alternatively, one may employ less sweetening agent if the same is desired, due to the fact that its primary function of masking the taste of the surfactant has been removed.

Broadly speaking, the instant invention includes the provision of a dentifrice containing a surfactant having the following general formula, $R-(OCH_2CH_2)_xOCH_2COOM$, wherein R is a $C_8-C_{18}$ alkyl chain, x is an integer of about 1-9 and M is selected from the group consisting of non-toxic alkali and alkaline earth metals, ammonium and $C_2$ to $C_3$ alkylol amines.

The surfactant which may appropriately be called an alkyl polyglycol ether carboxylate, generally, may be derived from natural fatty alcohols having straight chains or synthetic alcohols having branched chains. The chain length will generally be about 8-18, preferably about 10-16, or about 12-14. X may vary as aforesaid from about 1-9, preferably about 3-5, most commonly about 2-4. The said forming ion may be any of the non-toxic alkali or alkaline earth metals, i.e., sodium potassium, calcium, etc. Also operative are the ammonium salts and alkylol amines such as triethanolamine.

The material may be synthesized as is disclosed by Dr. J. G. Aalbers in "Lauryl (Poly-1-Oxapropene) Oxaethane Carboxylic Acids" published by Drukkeig Wed G. Van Soest N.W., Amsterdam, 1964. The material may be employed in the dental product in amounts of about 0.05 to about 4.0% by weight based on the total finished product.

The dentifrice formulation of the invention includes liquids and solids that are proportioned to form a creamy mass of desired consistency which is extrudible from an aerosol container or a collapsible tube (for example aluminium or lead). In general, the liquids in the dental cream will comprise chiefly water, glycerine, aqueous solutions of sorbitol, propylene glycol, polyethylene glycol 440, etc., including suitable mixtures thereof. It is advantageous usually to use a mixture of both water and a humectant or binder such as glycerine or sorbitol or both. The total liquid content will generally be about 20 to 75% by weight of the formulation. It is preferred to use also a gelling agent in dental creams and gels such as the natural and synthetic gums and gum-like materials, for example, Irish moss, gum tragacanth, methyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite CP and Laponite SP. These grades of Laponite have the formula $[Si_8Mg_{5.1}Li_{0.6}H_{7.6}O_{24}]^{0.6}Na^+$. The solid portion of the vehicle is usually present in an amount of up to about 10% preferably about 0.2 to 5% by weight of the formulation.

In the preparation of tooth powders, it is usually sufficient to admix mechanically, e.g., by milling, the various solid ingredients, in appropriate quantities and particle sizes.

In chewable dental tablets the solids and liquids are proportioned similarly to the amounts in dental creams and the surfactant is blended with the solids and liquids, a waxy matrix such as polyethylene glycol having a molecular weight of about 6,000 by weight, generally in amount of about 4–20% by weight is also employed in order to facilitate forming a tablet of desired size and shape.

In other oral preparations, such as mouthwash and the like, the carrier is an aqueous vehicle which may be included in amounts of about 20–99% by weight of the preparation. Typically, the vehicle also includes about 5–30% by weight of a non-toxic alcohol, such as theanol. Preferred mouthwashes generally will comprise approximately by weight (a) 65–85% water, (b) 5–25% non-toxic alcohol and (c) 0.5–3% of the surface-active agent; more preferably about 68–78% water and up to about 15% of at least one material selected from the group consisting of glycerine, sorbitol and propylene glycol and wherein said alcohol is denatured ethanol. Optimally, there will be present about 10–20% ethanol, 8–12% glycerine and about 0.01–2.0% of sweetener and/or flavor.

It is to be understood, that where desired, the instant surfactant may be used in combination with one or more of the conventionally used surfactants commonly found in oral products.

In this instance, the relative amounts of the two systems will be suitable adjusted as as to achieve the desired result, maintaining the total level within the limits aforementioned. Generally speaking, amounts of about 1:99 to 99:1 one relative to the other are satisfactory.

Organic surface-active agents that may be employed in conjunction with the instant surfactant may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride of hydrogenated coconut oil fatty acids, higher alkyl sulfates, such as sodium lauryl sulfate, alkyl aryl sulfonates, such as sodium dodecyl benezene sulfonate, higher alkyl sulfoacetates, higher fatty acid esters of 1,2-dihydroxy propane sulfonates, olefin sulfonates and the substantially saturated higher aliphatic acyl amides of lower aliphatic amino carboxylic acid compounds, such as those having 12–16 carbon atoms in the fatty acid, or acyl radicals, and the like. Examples of the last mentioned amides are N-lauroyl sarcosine, and the sodium, potassium and ethanol-amine salts of N-lauroyl, N-myristoyl, or N-palmitoyl sarcosine which should be substantially free from soap or similar higher fatty acid material which tends to substantially reduce the effect of these compounds. The use of these sarcosinate compounds in dentifrice compositions is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface active materials include nonionic agents such as condensates of sorbitan monostearate with approximately 60 moles of ethylene oxide, condensates of ethylene oxide with propylene oxide, condensates of propylene glycol ("Pluronics"), and amphoteric agents such as quaternized imidazole derivatives which are available under the trademark "Miranol" such as Miranol $C_2M$.

Other suitable nonionic detergents are the condensation products of an α-olefin oxide containing 10–20 carbon atoms, a polyhydric alcohol containing 2–10 carbons and 2–6 hydroxyl groups and either ethylene oxide or a heteric mixture of ethylene oxide and propylene oxide. The resultant detergents are heteric polymers having a molecular weight in the range of 400–1,600 and containing 40%–80% by weight of ethylene oxide, with an α-olefin oxide to polyhydric alcohol mole ratio in the range of about 1:1 to 1:3. These detergents are manufactured using well-known polymerization techniques under conditions of high temperature and high pressure. The olefin oxide and polyhydric alcohol usually are added to the reactor prior to the addition of ethylene oxide. These nonionic detergents may be mixed with similar nonionic detergents as well as other type detergents described herein.

The dental cream formulations will generally also include a dentally acceptable, substantially water insoluble, polishing agent of the type commonly employed in dental creams. Representative polishing agrnts include, for example, dicalcium phosphate, tricalcium phosphate, insoluble sodium metaphosphate, aluminum hydroxide, including hydrated alumina, colloidal silica, magnesium carbonate, calcium carbonate, calcium carbonate, calcium pyrophosphate, bentonite, etc., including suitable mixtures thereof. When employed, it is preferred to use the water insoluble phosphate salts as the polishing agents and more particularly insoluble sodium metaphosphate and/or a calcium phosphate such as dicalcium phosphate dihydrate in dental creams. When visually clear gels are employed, a polishing agent of colloidal silica, such as those sold under the trademark Syloid as Syloid 72 and Syloid 74 or under the trademark Santocel as Santocel 100 and synthetic alkali metal aluminosilicate complexes may be particularly useful, since they have refractive indices close to the refractive indices of gelling agent-liquid (generally including humcetants such as glycerine and sorbitol) systems commonly used in dentifrices. When employed, the total polishing agent conyent is generally in amounts from about 15 to 75% by weight in a dental cream. In a visually clear gel the total amount of polishing agent is generally from about 5 to 50% by weight.

Various other materials may be incorporated in the dentifrice formulations of this invention. Examples thereof are coloring or whitening agents or dyestuffs, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties and characteristics desired and are selected and used in proper amounts depending upon the particular type of preparation involved.

The compositions of the present invention may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), potassium fluorozirconate, sodium hexafluorostannate, stannous chlorofluoride, and sodium monofluorophosphate. These materials which dissociate or release fluorine-containing ions, suitably may be present in an effective but non-toxic amount usually within the range of about 0.1 to 1% by weight, based on the water soluble fluorine content thereof. Sodium fluoride, stannous fluoride, and sodium monofluorophosphate are particularly preferred, as well as mixtures thereof.

Antibacterial agents may also be employed in the oral preparation of the instant invention to provide a total content of such agents of up to about 5% by weight, preferably 0.01 to 5.0%, most preferably about 0.05-1.0%. Typical antibacterial agents include:

$N^1$-(4-chlorobenzyl)-$N^5$-(2,4dichlorobenzyl) biguandie;
p-chlorophenyl biguanide;
4-chlorobenzyhydryl biguanide;
4-chlorobenzyhydrylguanylurea;
N-3-lauroxypropyl-$N^5$-p-chlorobenzylbiguanide;
1-(lauryldimethylammonium)-8-(p-chlorobenzyl-dimethylammonium) octane dichloride;
5,6-dichloro-2-guanidinobenzimidazole;
$N^1$-p-chlorophenyl-$N^5$-laurylbiguanide;
1,6-di-p-chlorophenyl niguanidohexane;
1,6-bis(2-ethylhexyl biguanido) hexane;
5-amino-1,3-bis(2-ethylhexyl)-5-methylhexahydropyrimidine; and their non-toxic acid addition salts.

Synthetic finely divided pyrogenic silica such as those sold under the Trademark Cab-O-Sil M-5, Syloid 244, Syloid 266 and Aerosil D-200 may also be employed in amounts of about 1-5% by weight to promote thickening or gelling and to improve clarity of the dentifrice.

The taste of the new compositions may be modified by employing suitable flavoring or sweetening materials. Examples of suitable flavoring constituents include the flavoring oils, e.g., oil or spearmint, peppermint, wintergreen, sassafras, clove, sage, eucalyptus, marjoram, cinnamon, lemon and orange as well as sodium methylsalicylate. Suitable sweetening agents include sucrose, lactose, maltose, sorbitol, sodium cyclamate and perillartine as well as saccharine wherein desired. Suitable sweetening agents include sucrose, lactose, maltose, sorbitol, sodium cyclamate and perillartine as well as saccharine where desired. Suitably, flavor and sweetening agents may together comprise from 0.01-5% or more of the compositions of the instant invention. Additionally, the new dental formulations can be provided with the unusual biting flavor of chloroform. Accordingly, instead of or in addition to the foregoing flavoring or additional sweetening materials, the new formulation can include up to about 5%, preferably between 0.1 and 5% by weight of chloroform and chloroform flavoring.

It is desirable that the pH of the dental cream formulations be in the range of about 3 to 10 which may be accomplished where necessary by employing such acids as citric, acetic, chloropropionic, malonic, formic, fumaric, methoxyacetic, and propionic of salts thereof. Lower pH's than 3 are generally undesirable for oral use. When stannous ions are present, the pH is preferably lower than about 5. The preferred pH range is 3.5 to about 5.0 when stannous ions are present and about 4.5 to about 7.0 in the absence of stannous ion.

The following specific examples are further illustrative of the nature of the present invention but it is understood that the invention is not limited thereto. Dental cream formulations are prepared in the usual manner, except as indicated, and all amounts and proportions are by weight except as otherwise indicated.

EXAMPLE 1 — DENTAL CREAM

| | % |
|---|---|
| Glycerine | 9.474 |
| Sorbitol | 17.000 |
| Carboxymethylcellulose (Na salt) | 1.100 |
| Na Benzoate | 0.500 |

-continued

| | % |
|---|---|
| $C_{12}(OCH_2CH_2)_2$—$OCH_2COONa$ | 2.000 |
| Sodium saccharin | 0.2 |
| Water | to 100 |
| $Na_2PO_3F$ | 0.760 |
| $TiO_2$ | 0.400 |
| Insoluble Na Metaphosphate | 41.850 |
| Anhydrous dicalcium phosphate | 5.000 |
| Alumina - Hydrated | 1.000 |
| Flavor | 1.000 |
| | 100.00 |

EXAMPLE 2 — DENTAL CREAM

| | Parts |
|---|---|
| Antimicrobial agent | 0.1 |
| Sodium benzoate | 0.15 |
| $C_{14}(OCH_2CH_2)_3$—$OCH_2COOK$ | 2.00 |
| Sodium saccharine | 0.2 |
| Insoluble sodium metaphosphate | 40.6 |
| Dicalcium phosphate dihydrate | 5.0 |
| Titanium dioxide | 0.4 |
| Stannous fluoride | 1.4 |
| Gum tragacanth | 1.0 |
| Oil of wintergreen | 1.0 |
| Color | 0.03 |
| Water | to 100 |
| Glycerine (99.3%) | 27.10 |

This composition is used by brushing the teeth therewith at least once daily.

In the above dental cream, sodium lauryl sulfate or sodium-N-lauroyl sarcosinate, may be employed in part for the instant surfactant.

EXAMPLE 3 — DENTAL CREAM

| | Parts |
|---|---|
| Antimicrobial agent | 0.1 |
| Sodium benzoate | 0.5 |
| Tetrasodium pyrophosphate | 0.25 |
| Dicalcium phosphate dihydrate | 36.75 |
| Calcium carbonate | 5.0 |
| Sodium carboxymethylcellulose | 0.75 |
| $C_{16}(OCH_2CH_2)_5OCH_2COOCa$ | 2.00 |
| Glycerine (99.3%) | 23.95 |
| Oils of peppermint and spearmint, 1:1 | 0.8 |
| Water | to 100 |

EXAMPLE 4 — TRANSPARENT CREAM

| | Parts |
|---|---|
| Glycerine | 25.00 |
| Sodium carboxymethylcellulose | 0.70 |
| $C_{16}(OCH_2CH_2)_5OCH_2COOCa$ | 2.0 |
| Sodium benzoate | 0.50 |
| Sorbitol (70%) | 44.83 |
| Water | to 100 |
| Sodium aluminum silicate | 16.00 |
| Syloid 244 | 5.00 |
| Flavor | 1.00 |
| Sodium lauryl sulfate | 2.00 |

EXAMPLE 5 — CHLOROFORM CONTAINING CREAM

| Components | Parts |
|---|---|
| Glycerine | 22.00 |
| Carboxymethyl cellulose (Na salt) | 0.80 |
| Tetrasodium Pyrophosphate | 0.25 |
| Sodium benzoate | 0.50 |
| $C_{12}(OCH_2CH_2)_4OCH_2COONa$ | 2.0 |
| $H_2O$ | 20.95 |
| Dicalcium phosphate . $_2H_2O$ | 46.00 |

-continued

| Components | Parts |
| --- | --- |
| Calcium carbonate | 5.50 |
| Flavor oil | 1.00 |
| Chloroform | 1.00 |
| | 100.00 |

EXAMPLE 6 — CLEAR CREAM

The following visually clear dental cream is prepared:

| Components | Parts |
| --- | --- |
| Sorbitol (70%) | 75.0 |
| Glycerine | 25.1 |
| Laponite SP | 2.0 |
| $C_{10}OCH_2CH_2)_1OCH_2COONa$ | 2.0 |
| Aerosil D200 | 5.0 |
| Sodium aluminosilicate | 16.0 |
| Flavor | 1.0 |
| Color | 1.0 |
| Water | 20.0 |

The sodium aluminosilicate employed is a complex having a refractive index of 1.46, a moisture content of about 6%, an average particulate size of about 35 microns and a sieve loose bulk density of about 0.07 g./cc.

EXAMPLE 7 — MOUTH RINSE

| | Parts |
| --- | --- |
| Antimicrobial agent | 0.1 |
| $C_{12}(OCH_2CH_2)_4OCH_2COONa$ | 0.6 |
| Saccharin | 0.035 |
| Alcohol | 14.78 |
| Water | 83.87 |
| Color | 0.04 |
| Oil of lemon | 0.50 |

This composition is used by rinsing of the oral cavity with about 10 cc. thereof once or more often

EXAMPLE 8 — CHEWABLE TABLET FOR BRUSHING

| | Parts |
| --- | --- |
| Insoluble sodium metaphosphate | 32.59 |
| Dicalcium phosphate dihydrate | 4.03 |
| Poly(ethylene glycol) having a molecular weight of about 6,000 | 5.00 |
| Na Saccharine | 0.25 |
| Sodium carboxymethylcellulose | 1.25 |
| $C_{15}(OCH_2CH_2)_8OCH\ COONa$ | 2.25 |
| Starch | 3.0 |
| Mannitol | 47.3 |
| Talc | 0.5 |
| Magnesium stearate | 1.25 |
| Flavor, color, etc. | 2.48 |
| Antimicrobial agent | 0.1 |

The tablet is employed as a dentifrice by introducing into the mouth a tablet thereof having a weight of about 0.5 grams, crushing it between the teeth, and then brushing the teeth in the usual fashion with saliva acting as a fluid vehicle, for the crushed tablet particles.

Although the foregoing specific examples include preferred and typical formulations, they should not be taken as limitations on the invention. Accordingly, reference should be made to the following claims in determining the full scope of the invention.

What is claimed is:

1. A dental cream dentifrice free from bitter taste of surfactant comprising about 15–75% by weight a water-insoluble dental polishing agent in a dental cream vehicle and containing therein as the essential surfactant about 0.05–5.0% by weight of a substantially tasteless surfactant having the general formula, $R(OCH_2CH_2)_x\text{-}OCH_2COOM$, wherein R is a $C_{8-18}$ alkyl, x is an integer of about 1–9 and M is selected from the group consisting of non-toxic alkali and alkaline earth metals, ammonium and $C_2$ to $C_3$ alkylol amines.

2. A dentifrice as defined in claim 1 wherein M is selected from potassium, calcium and sodium.

3. A dentifrice as defined in claim 1 wherein x is about 2–5.

4. A dentifrice as defined in claim 1 wherein R is about 12–18.

5. A dentifrice as defined in claim 1 additionally consisting of flavoring oils, sweetening agents and mixtures thereof.

6. A dentifrice as defined in claim 1 further containing a fluorine compound having a beneficial effect on the care and hygiene of the oral cavity in an effective but non-toxic amount.

7. A dentifrice as defined in claim 6 wherein said fluorine containing compound is selected from the group consisting of sodium fluoride, stannous fluoride, potassium fluoride, potassium stannous fluoride, sodium hexafluorostannate, stannous chlorofluoride, sodium fluorozirconate and sodium monofluorophosphate.

8. A packaged dispensable dental product comprising a walled container having therein a measured amount of the dentifrice as defined in claim 1.

9. A mouthwash free from bitter taste of surfactant comprising an aqueous alcohol vehicle containing about 5–30% by weight of a non-toxic alcohol and containing therein as the essential surfactant about 0.05–5.0% by weight of a substantially tasteless surfactant having the general formula, $R(OCH_2CH_2)_xOCH_2COOM$, wherein R is a $C_{8-18}$ alkyl, x is an integer of about 1–9 and M is selected from the group consisting of non-toxic alkali and alkaline earth metals, ammonium and $C_2$ to $C_3$ alkylol amines.

10. A dentifrice as defined in claim 9 further containing an effective amount of an antibacterial agent.

11. A mouthwash as defined in claim 9 containing approximately by weight (a) 65–85% water, (b) 5–25% non-toxic alcohol and (c) 0.5–3% of said surface-active agent.

12. A mouthwash as defined in claim 9 containing about 68–78% water and up to about 15% of at least one material selected from the group consisting of glycerine, sorbitol and propylene glycol and wherein aaid alochol is denatured ethanol.

13. A mouthwash as defined in claim 12 containing about 10–20% ethanol, 8–12% glycerine and about 0.01–.6% of said surfactant.

14. A chewable dental tablet free from bitter taste of surfactant comprising about 15–75% by weight of water-insoluble dental polishing agent in a waxy matrix and containing therein as the essential surfactant about 0.05–5.0% by weight of a substantially tasteless surfactant having the general formula, $R(OCH_2CH_2)_xOCH_2COOM$, wherein R is a $C_{8-18}$ alkyl, x is an integer of about 1–9 and M is selected from the group consisting of non-toxic alkali and alkaline earth metals, ammonium and $C_2$ to $C_3$ alkylol amines.

* * * * *